United States Patent [19]

Lingenhöle et al.

[11] 4,021,919
[45] May 10, 1977

[54] DENTAL HANDPIECE OPERABLE BY COMPRESSED AIR

[75] Inventors: Bernhard Lingenhöle, Biberach an der Riss, Germany; Richard R. Stephens, Brisbane, Australia

[73] Assignee: Kaltenbach & Voigt, Biberach an der Riss, Germany

[22] Filed: May 6, 1976

[21] Appl. No.: 683,945

[30] Foreign Application Priority Data

May 13, 1975 Germany .......................... 2521314

[52] U.S. Cl. .................................. 32/27; 415/503
[51] Int. Cl.² .................................. A61K 5/02
[58] Field of Search ................ 415/12, 503; 32/27, 32/26

[56] References Cited

UNITED STATES PATENTS

| 3,218,028 | 11/1965 | Borden | 32/27 |
| 3,639,074 | 2/1972 | Killick | 415/503 |

*Primary Examiner*—Robert Peshock

[57] ABSTRACT

A dental handpiece operable by compressed air having a turbine rotor, a drive sleeve for holding a dental instrument and coupled with the rotor by a ball-type planetary transmission, and an adjustment member operable on the planetary transmission so as to increase the torque transmissible by the planetary transmission. The transmission comprises inner and outer rings, with the balls frictionally engaged therebetween, the balls being in drive transmitting relationship with the rotor or the drive sleeve. A first of the rings is non-rotatable and a second of the rings is coupled with whichever of the rotor or drive sleeve is not associated with the balls. One of the rings is axially moveable relative to the other ring by the adjustment member in order to increase the radial load applied between the inner and outer rings through the intermediary of the balls whereby the torque transmitted by the planetary transmission can be increased. A pressure chamber is defined on one side of the adjustment member and receives a supply of compressed air in order to move the adjustment member with consequential axial movement of said one ring.

12 Claims, 10 Drawing Figures

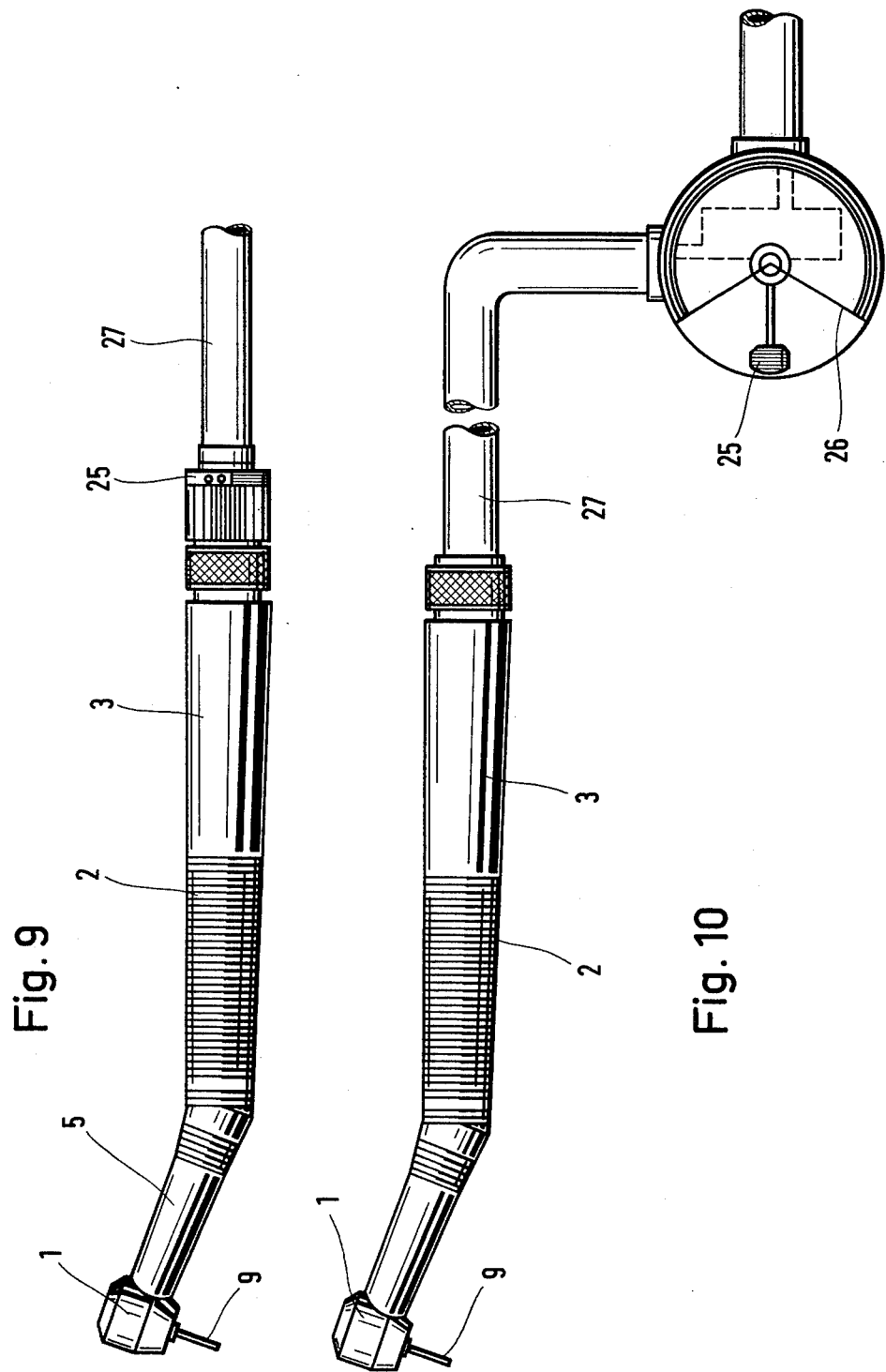

DENTAL HANDPIECE OPERABLE BY COMPRESSED AIR

This invention relates to a dental handpiece operable by compressed air and comprising:
a turbine rotor forming a first drive element;
a driving air line arranged to supply compressed air to the rotor to drive the latter;
a second drive element coupled with said rotor and arranged to hold, and to drive, a dental instrument when the latter is coupled with the second drive element;
a ball-type planetary transmission coupling together the first and second drive elements;
and an adjustment member operable on the planetary transmission to increase the torque transmissible by the planetary transmission.

A dental handpiece of the above type is known from German specification No. 1,055,752. In the case of this known handpiece, there is associated with an axially displaceable adjustment pusher, designed as a displacement ring, an outwardly curved leaf spring which is fixed at one of its ends, extends in the longitudinal direction of the handpiece and, for example in the case of increased loading of the dental instrument and therewith requirement for increased torque, has to be manually compressed so that there takes place elongation of the leaf spring. Thereby, the spring presses through the agency of its unfixed end against the displacement ring, whereby the latter is, whilst overcoming the force of a helical spring, displaced towards an axially displaceable but non-rotatable outer ring of the ball-planetary transmission and displaces the outer ring relative to the inner ring for the purpose of adjusting the balls, so as to increase the torque transmitted. The springs, i.e., the leaf spring and the helical spring, represent supplementary components which are subjected to a risk of wear and the functioning of which can be disturbed due to penetration of dust or dirt into the travel path of the springs. To this must be added the fact that the springs have varying characteristic lines and that the displacement which is a function of the spring travel path of the axially displaceable outer ring, and therewith the adjustment of the balls, in consequence of the inertia of the springs, is initiated only subsequent to actuation of the leaf spring and, therewith, in chronologically delayed fashion relative to the commencement of increased loading of the instrument.

It is an object of the invention to provide an improved dental handpiece of the type initially described in which the risk of wear and also of function impairment is reduced, compared with the known dental handpiece, and wherein adjustment of the balls of the planetary transmission can take place with maximum rapidity.

According to the invention there is provided a dental handpiece operable by compressed air and comprising:
a turbine rotor forming a first drive element;
a driving air line arranged to supply compressed air to the rotor to drive the latter;
a second drive element coupled with said rotor and arranged for holding a dental instrument in order to drive the latter when the second element is driven by the rotor;
a planetary transmission coupling together the first and second drive elements, said transmission comprising an outer ring, an inner ring, and balls located between and frictionally engageable with said inner and outer rings; said balls being in drive transmitting relationship with one of said drive elements, and a first of said rings being non-rotatably mounted in the handpiece and a second of said rings being coupled with the other of said drive elements for rotation therewith; and one of said rings being mounted for axial movement in the handpiece relative to the other ring in order to increase the radial load applied between the rings through the intermediary of the balls so as to increase the torque transmissible by the planetary transmission;
an adjustment member moveably mounted for engagement with said one ring in order to move the latter axially;
and a chamber defined in the handpiece, on one side of said adjustment member, for effecting movement of the adjustment member with consequential axial movement of said one ring so as to increase the torque transmissible by the planetary transmission when compressed air is supplied to said chamber.

The adjustment member may comprise a displacement ring arranged in, for example, an annular chamber in the manner of a piston or rotary piston (or annular piston) and which is displaced solely due to the compressed air fed to the chamber so that it becomes unnecessary to employ springs for this purpose and any risk, which would result therefrom, of wear and impairment of functioning is eliminated. The pressure air fed to the chamber sets the displacement ring practically immediately in motion, so that, again practically immediately, the axially displaceable ring is displaced and the balls are adjusted whilst increasing their application pressure.

It is expedient if, for subjecting the chamber to the action of pressure air, there debouches into the chamber on the side of the displacement ring remote from the axially displaceable ring a control air line branching-off from the driving air line. Thereby, especially rapid, direct and undelayed adjustment of the balls is achieved as a function of the drive air pressure.

Since, due to the interposed planetary transmission, the first and second drive elements rotate at different speeds, it is preferred to arrange additionally to the bearing constituted by the planetary transmission, between the two drive elements, at least one further bearing (expediently a ball bearing) compensating for the differing velocities. If the inner ring of the planetary transmission is arranged on the rotor to be rotatable therewith, the supplementary bearing acts as counterforce to the adjusting forces of the planetary transmission.

The inner ring or outer ring rotatable in each particular instance with one of the drive elements can be arranged to be axially displaceable on this drive element under the action of the displacement ring. For this purpose, such an inner ring or outer ring may be provided with radially extending drive or entrainment means engaging into an elongate groove formed in the drive element.

In order to avoid the friction occurring thereby between the displacement ring on the one hand and the inner ring or outer ring on the other hand, instead of this arrangement the outer ring or inner ring which is non-rotatable in each particular instance may be arranged to be axially displaceable under the action of the displacement pusher. For this purpose, it is advantageous if the non-rotatable outer ring or the non-rotatable inner ring of the planetary transmission bears, via at least one resilient damping ring, against the non-rotatable parts of the handpiece. The damping rings make possible the desired axial displacement of the outer ring or inner ring and serve for taking up the radial torque and also for damping the oscillations. With this arrangement, direct contacting of the displacement ring or pusher with the outer ring or inner ring can be prevented when the displacement pusher passes into abutment at one of the damping rings. For this purpose, in order to achieve satisfactorily damped displacement transmission from the displacement pusher to the outer ring or inner ring, it is preferred that at least that damping ring against which the displacement pusher passes into abutment is partially housed or let into a wall of the outer ring or inner ring facing the non-rotatable parts of the handpiece.

To the extent that the damping ring against which the displacement pusher passes into abutment projects axially beyond the end face of the outer ring or of the inner ring facing the displacement pusher, an especially simple form of design is achieved, since the displacement pusher is then not required to possess any elements extending into the gap available between the outer ring or inner ring and the non-rotatable parts of the handpiece, so as to be able to act, via the damping ring, on the outer ring or the inner ring.

In particular when the displacement pusher is designed as displacement ring, the damping ring and the displacement pusher may advantageously be in one piece and be made for example from rubber.

In pre-determined cases of instrument loading, the air accumulation arising in the turbine chamber when the turbine rotor is running at low speed or is at a standstill may give rise to an increased air feed through the control air line and therewith automatic adjustment of the balls of the planetary transmission, whereby also the required torque increase may occur. For those loading cases to which this does not apply, it is proposed that the quantity per unit time and/or the pressure of the air acting on the chamber containing the adjustment member may be adjustable.

Expediently, the adjusting or setting means for this purpose is arranged in the driving air line upstream of the branching-off of the control air line since, in contradistinction to the arrangement of the setting means in the control air line, also the turbine rotor is subjected to stonger action.

BRIEF DESCRIPTION OF THE DRAWINGS

FIG. 9 is a side view of an entire dental handpiece; and

FIG. 10 is a view, similar to FIG. 9, of an entire dental handpiece connected to a compressed air supply line having a pedal control switch.

DESCRIPTION OF PREFERRED EMBODIMENTS

Referring first to FIGS. 9 and 10 of the drawings, there are shown a dental handpiece 2, a holding or grasping sleeve 3, and a head 1 which may be angled relative to the sleeve 3. Although the illustrated head 1 is an angled head, the head 1 and the sleeve 3 may be coaxially arranged, thereby providing a straight handpiece. A dental instrument 9 is releasably coupled with the head 1, and a driving air supply line 5 is arranged to provide a supply of compressed air to drive a turbine rotor in the head 1.

Figure 1:
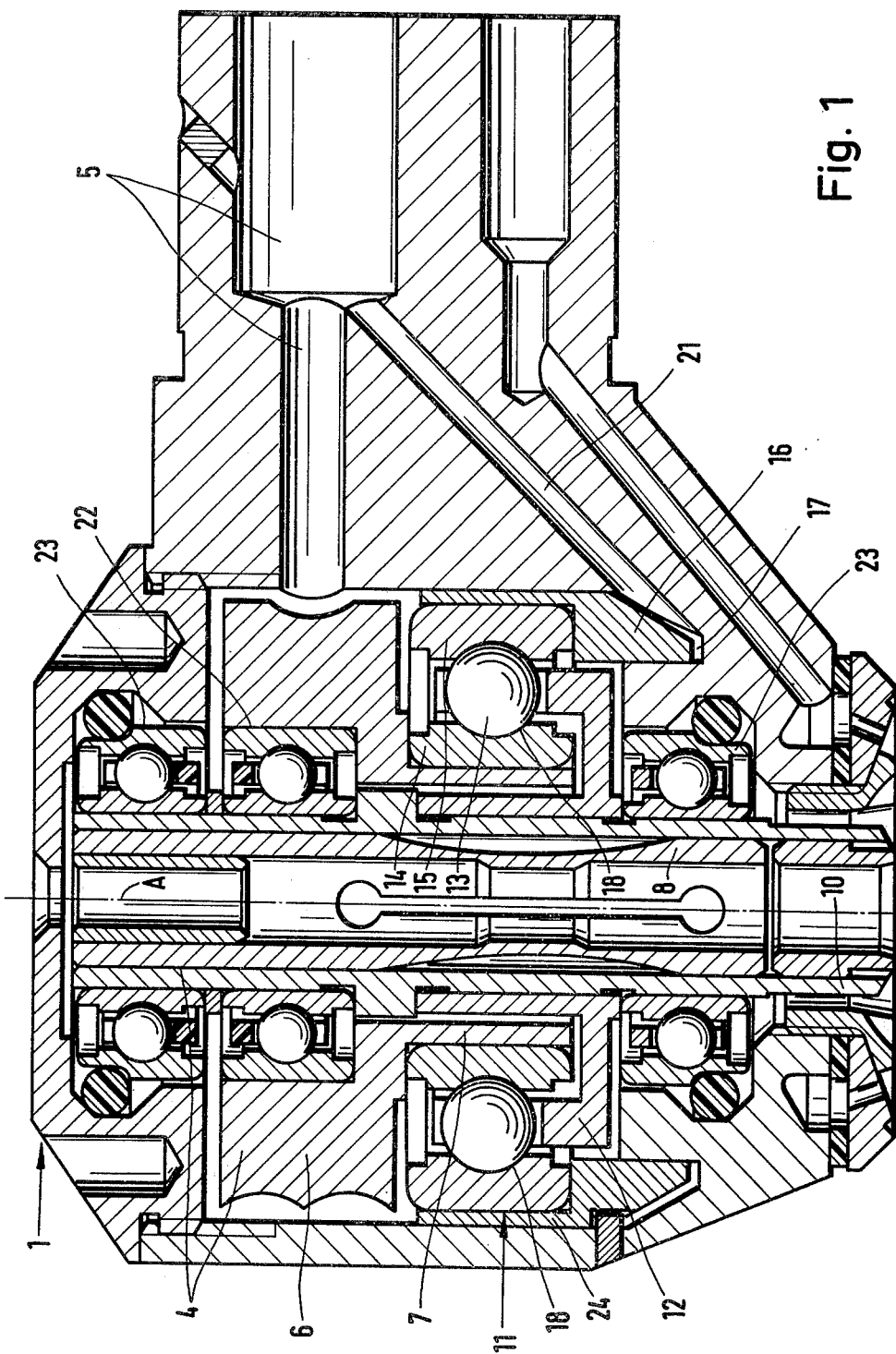
FIG. 1 is a longitudinal sectional view of the head of a dental handpiece.

Referring now to FIG. 1 of the drawings, one construction of head 1 is shown in more detail, and comprises a two-part drive shaft 4 which compreses, as a first drive element, a turbine rotor 7 having blades or vanes 6 and adapted to be driven when pressure air is supplied thereto via driving air line 5. A second drive element of shaft 4 is comprised by a drive sleeve 10 which is coupled with rotor 7 and is adapted to hold, and to drive, a dental instrument 9 by means of a clamping device or tongs 8. By way of example, the dental instrument 9 may be a dental drill.

The first drive element 7 and the second drive element 10 are arranged co-axially, and are coupled together by means of a ball-type planetary transmission 11. Various examples of planetary transmission will be described in more detail below, with reference to FIGS. 5 to 8. The diagrammatic illustration in FIG. 5 corresponds to the detailed constructions illustrated in FIGS. 1 and 2, in which gearing down from first element 7 to second, driven element 10 is in the ratio of approximately 3:1.

The planetary transmission 11 shown in FIG. 1 comprises an inner ring 14 which is fixed to drive element 7 for rotation therewith, an outer ring 15 which is non-rotatably mounted in the handpiece, and balls 13 frictionally engaging between the inner ring 14 and outer ring 15. As well as being non-rotatably mounted in the handpiece, outer ring 15 is also axially moveable relative to inner ring 14, for a purpose described in more detail below. Matching grooves 18 are formed in the rings 14 and 15 for accommodating the balls 13.

The planetary transmission 11 also includes a fork-shaped cage 12 which is arranged coaxially with the common axis A of the drive elements 7 and 10. The parallel limbs of the cage 12 engage between the balls 13. As described above, the balls 13 frictionally engage between the inner ring 14 and outer ring 15 and, since outer ring 15 is non-rotatable, rotation of first drive element 7 will effect rotation of the inner ring 14 therewith, which imparts rotation to the balls 13 whereby the cage 12 is rotated, and therefore also the second drive element 10 is rotated.

Although the balls 13 have frictional engagement between the inner ring 14 and outer ring 15, the torque transmission capacity of the planetary transmission 11 may be increased by moving outer ring 15 axially relative to inner ring 14. Such movement of the outer ring 15 brings about an increased radial load between the inner ring 14 and outer ring 15 through the intermediary of the balls 13, so that there is a greater frictional engagement between the balls 13 and the rings 14 and 15, whereby a greater torque can be transmitted by the transmission 11. To achieve this axial movement of outer ring 15, an adjustment member is provided in the form of a displaceable pusher ring 16. The adjustment ring 16 is arranged in an annular chamber 17, and a branch line 21 taken from driving air line 5 communicates with chamber 17. Upon the supply of compressed air through branch line 21, adjustment ring 16 is urged axially towards outer ring 15, and thereby moves the latter axially so as to increase the torque transmission capacity of the planetary transmission 11.

Although the planetary transmission 11 constitutes bearing for the first drive element 7 and second drive element 10, it is preferred that one or more additional bearings shall be provided. As shown in FIG. 1, ball bearings 22 and 23 are provided.

In order to minimize the abutment between the displacement ring 16 and the outer ring 15, the ring 16 may be formed in one piece with a resilient annular damping portion 24.

Figure 2:
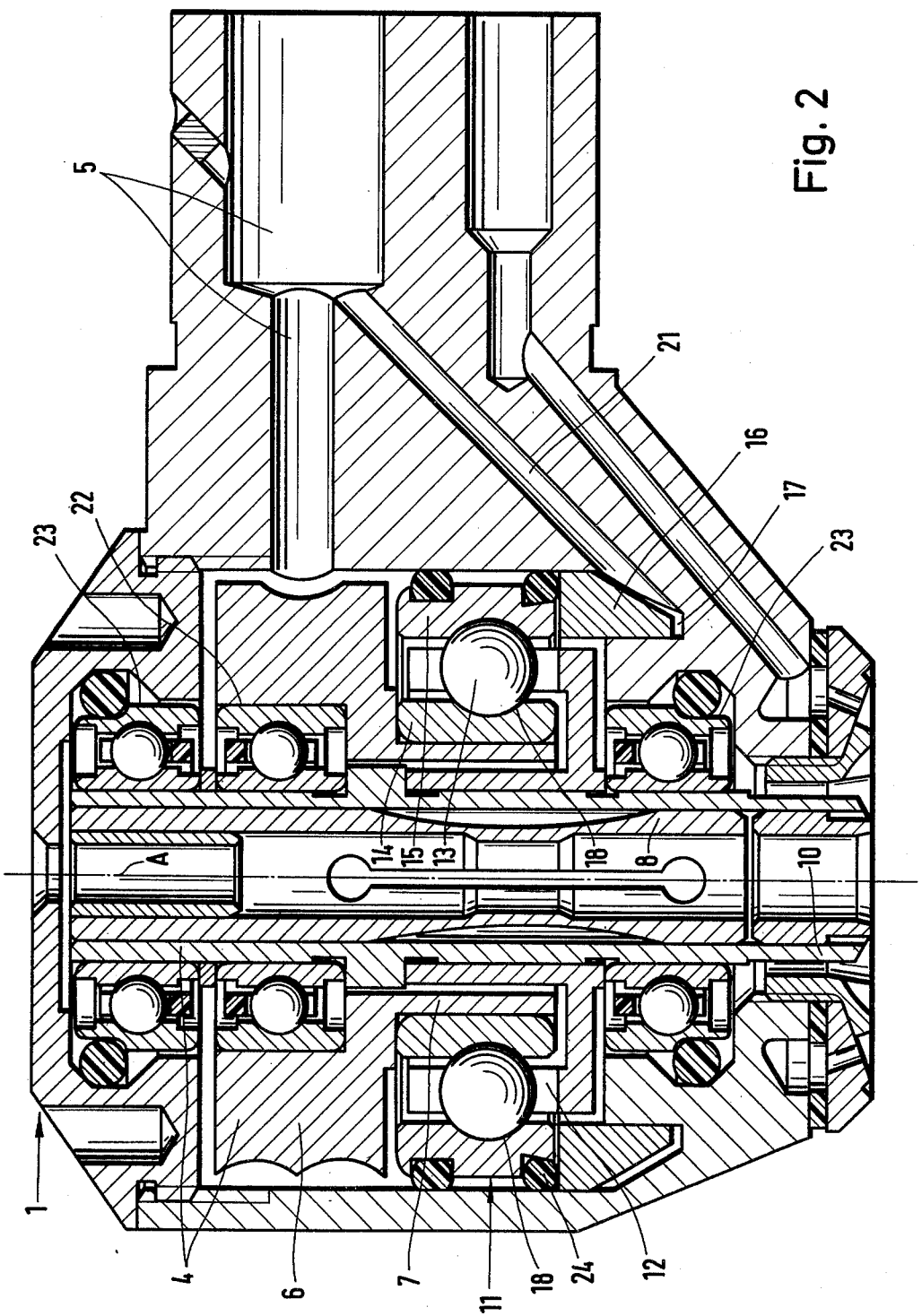
FIG. 2 to 4 are views, similar to FIG. 1, of further arrangements of head for a dental handpiece.

Referring now to FIG. 2 of the drawings, parts corresponding with the arrangement in FIG. 1 are designated by the same reference numerals, and will not be described in detail again. In the arrangement of head shown in FIG. 2, the outer ring 15 is again non-rotatable, and is mounted for axial movement relative to inner ring 14. Further, as in FIG. 1, the inner ring 14 is mounted for rotation with the rotor or first drive element 7. In order to cushion the abutment of the adjustment ring 16, resilient damping rings 24 are provided between stationary parts of the handpiece and the outer ring 15. Two damping rings 24 are provided, and each is housed or let into the outer wall of the outer ring 15 facing the stationary parts of the handpiece. One of the rings 24 is located adjacent the end face of ring 15 which faces the ring 16. Furthermore, this ring 24 projects axially towards the ring 16.

Figure 3:
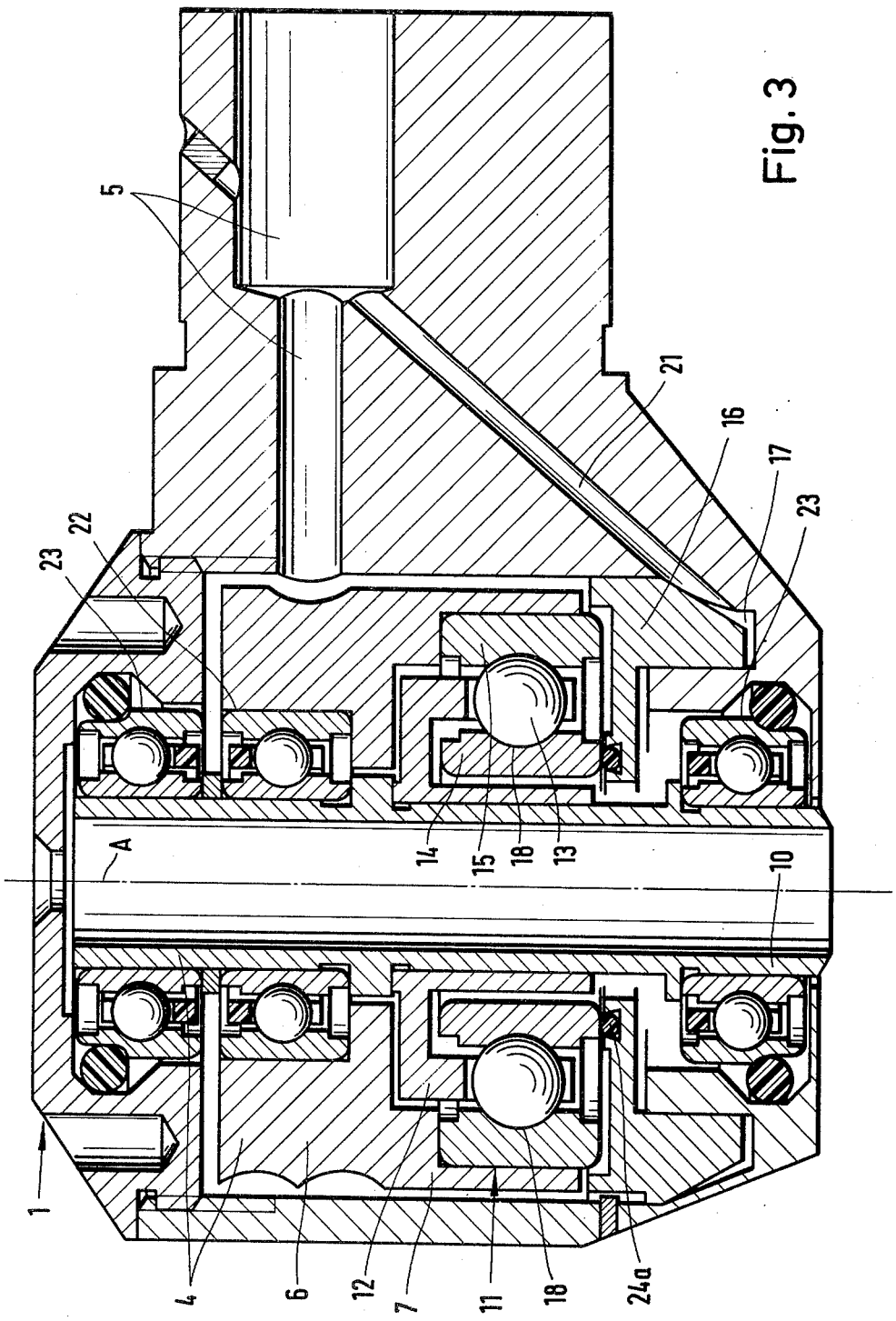

Referring now to FIG. 3, this arrangement differs in that it is the inner ring 14 which is non-rotatable, whereas the outer ring 15 is mounted for rotation with one of the drive elements (7 or 10), namely the drive element 7. Furthermore, the inner ring 14 is the axially moveable ring. Somewhat similarly to the arrangements of FIGS. 1 and 2, displacement ring 16 is arranged to effect axial movement of the moveable ring, but since in this arrangement it is the inner ring 14 which is axially moveable, ring 16 has an annular flange extending inwardly towards axis A, and is engageable with inner ring 14 via a resilient damping ring 24a let into, or housed in the annular flange of ring 16.

To transmit rotation from drive element 7 to drive element 10, the planetary transmission 11 has cage 12 in driving engagement with drive element 10. However, the cage 12, which is generally T-shaped in longitudinal cross-section, is reversed in position relative to axis A as compared with the arrangement in FIGS. 1 and 2.

Figure 4:
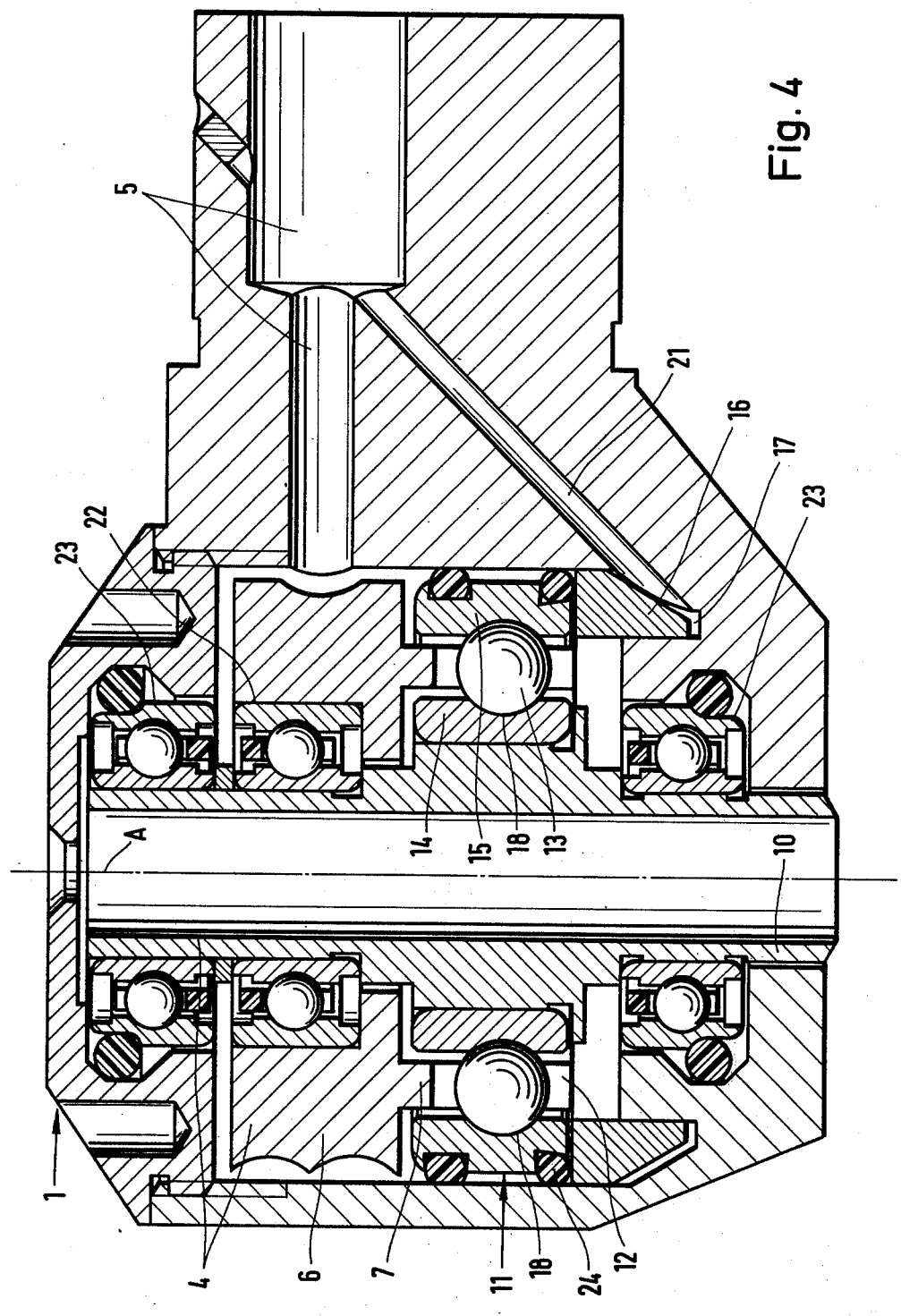

Referring now to FIG. 4, the outer ring 15 again is the non-rotatable ring, and is also axially moveable. The inner ring 14 is coupled drivingly with the second drive element 10, and the cage 12 is coupled with the first drive element 7 to be driven thereby. The outer ring 15 has resilient damping rings 24 in similar manner to that described with reference to FIG. 2.

Figure 5:
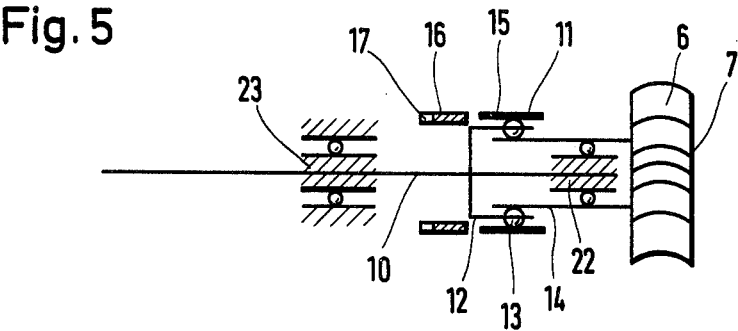
FIGS. 5 to 8 are diagrammatic illustrations of different arrangements of ball-type planetary transmission for coupling together a rotor, and an instrument-hold and drive sleeve, in the head of a dental handpiece.
Figure 6:
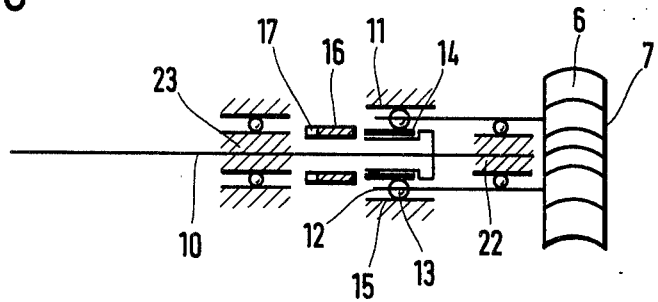

Referring now to FIGS. 5 to 8 of the drawings, diagrammatic illustrations are provided illustrating different means by which drive is transmitted from first drive element 7 to second drive element 10 via the ball-type planetary transmission 11. Parts corresponding with the parts described in FIGS. 1 to 4 are designated by the same reference numerals. In FIG. 5, the inner ring 14 is rotatable with first drive element 7, the outer ring 15 is non-rotatable and also axially moveable by adjustment ring 16, and the cage 12 is coupled with second drive element 10 to impart rotation thereto.

The arrangements described in FIGS. 1 to 5 all provide a ball-type planetary transmission having a non-rotatable ring which is also axially moveable, and the other ring being coupled with one of the drive elements (7, 10). However, as will be described below with reference to FIGS. 6 to 8, further arrangements of planetary transmission are provided in which one of the rings is non-rotatable, whereas the other ring is both rotatable and axially moveable. Thus, in FIG. 6, outer ring 15 is non-rotatable, whereas inner ring 14 is both rotatable and axially moveable. Drive is transmitted from first drive element 7 to the cage 12, whereby drive is transmitted to the inner ring 14 which, in turn, drives the second drive element 10. The inner ring 14 is mounted slideably on a sleeve, and is axially moveable thereon by means of the adjustment ring 16.

Figure 7:
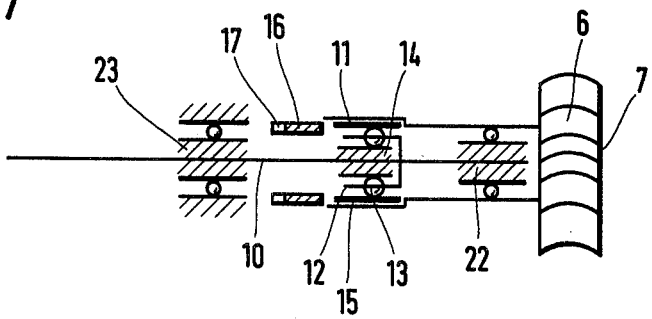

In FIG. 7, the inner ring 14 is non-rotatable, whereas the outer ring 15 is both rotatable and axially moveable. As shown, drive can be transmitted from first drive element 7 to the outer ring 15, and this effects the transmission of drive to second drive element 10 by way of cage 12 coupled therewith, since the inner ring 14 is non-rotatable.

Figure 8:
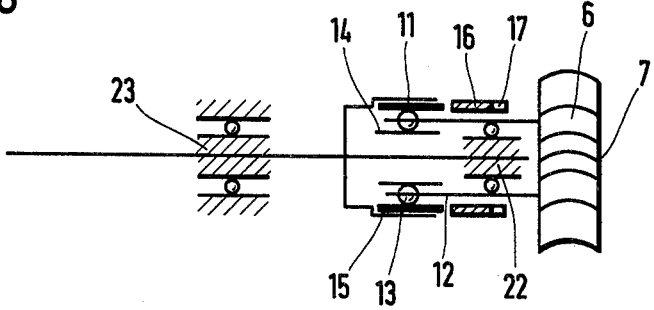

In FIG. 8, the inner ring 14 is non-rotatable, the outer ring 15 is both rotatable and axially moveable, and drive is transmitted to the planetary transmission 11 from first drive element 7 through cage 12. Thus, rotation of cage 12, with inner ring 14 non-rotatable, will effect rotation of outer ring 15 which is mounted within and in drive engagement with a sleeve coupled with second drive element 10.

Thus, as will be evident from the foregoing disclosure, each ball-type planetary transmission comprises an outer ring, an inner ring, and balls located between and frictionally engageable with the inner and outer rings, the balls being in drive transmitting relationship with one of the drive elements. Further, a first of the rings is non-rotatably mounted in the handpiece and a second of the rings is coupled with the other of the drive elements for rotation therewith. One of the rings (either the non-rotatable or the rotatable ring) is mounted for axial movement in the handpiece relative to the other ring in order to increase the radial load applied between the rings through the intermediary of the balls so as to increase the torque transmissible by the planetary transmission. An adjustment member is moveably mounted for engagement with the axially moveable ring, and a chamber is defined in the handpiece, on one side of the adjustment member, for effecting movement of the adjustment member with consequential axial movement of the axially moveable ring, so as to increase the torque transmissible by the planetary transmission when compressed air is supplied to the chamber.

We claim:

1. A dental handpiece operable by compressed air and comprising;

a turbine rotor forming a first drive element;

a driving air line arranged to supply compressed air to the rotor to drive the latter;

a second drive element coupled with said rotor and arranged for holding a dental instrument in order to drive the latter when the second element is driven by the rotor;

a planetary tranasmission coupling together the first and second drive elements, said transmission comprising an outer ring, an inner ring, and balls located between and frictionally engageable with said inner and outer rings; said balls being in drive transmitting relationship with one of said drive elements, and a first of said rings being non-rotatably mounted in the handpiece and a second of said rings being coupled with the other of said drive elements for rotation therewith; and one of said rings being mounted for axial movement in the handpiece relative to the other ring in order to increase the radial load applied between the rings through the intermediary of the balls so as to increase the torque transmissible by the planetary transmission;

an adjustment member moveably mounted for engagement with said one ring in order to move the latter axially;

and a chamber defined in the handpiece, on one side of said adjustment member, for effecting movement of the adjustment member with consequential axial movement of said one ring so as to increase the torque transmissible by the planetary transmission when compressed air is supplied to said chamber.

2. A dental handpiece according to claim 1, comprising a control line branching-off from said driving air line and communicating with said chamber.

3. A dental handpiece according to claim 1, including at least one bearing arranged between said first and second drive elements.

4. A dental handpiece according to claim 3, in which said bearing comprises a ball bearing.

5. A dental handpiece according to claim 1, comprising at least one annular resilient damping element interposed between said one ring and a fixed part of the handpiece.

6. A dental handpiece according to claim 5, in which said adjustment member is engageable with said one ring through the intermediary of said resilient damping element.

7. A dental handpiece according to claim 6, in which said resilient damping element is housed at least partly in a recess defined in said one ring.

8. A dental handpiece according to claim 7, in which said resilient damping element projects axially of an end face of said one ring and towards said adjustment member.

9. A dental handpiece according to claim 5, in which said resilient damping element and said one ring are of one-piece construction.

10. A dental handpiece according to claim 1, including control means for controlling a parameter of the supply of compressed air to said chamber.

11. A dental handpiece according to claim 10, in which said control means is arranged in said driving air line for controlling the rate of supply of compressed air.

12. A dental handpiece according to claim 10, in which said control means is arranged in said driving air line for controlling the pressure of the supply of compressed air.

* * * * *